United States Patent [19]

Seeley

[11] 4,094,648
[45] June 13, 1978

[54] URINE SPECIMEN CONTAINER

[75] Inventor: Leonard Seeley, Palatine, Ill.

[73] Assignee: Plastofilm Industries, Inc., Wheaton, Ill.

[21] Appl. No.: 763,250

[22] Filed: Jan. 28, 1977

[51] Int. Cl.² .............. A61B 10/00; B65D 23/00; G01N 1/10; G01N 33/16
[52] U.S. Cl. .................... 23/259; 4/144.2; 73/426; 73/427; 128/2 F; 195/139; 215/6
[58] Field of Search ............. 23/259; 73/426, 427; 128/2 F; 215/6

[56] References Cited

U.S. PATENT DOCUMENTS

| 3,748,099 | 7/1973 | Horlach | 23/259 |
| 3,774,455 | 11/1973 | Seidler | 23/259 X |
| 3,859,671 | 1/1975 | Tomasello | 128/2 F |
| 3,881,465 | 5/1975 | Raitto | 128/2 F |
| 3,888,236 | 6/1975 | Marx | 73/427 |
| 3,894,845 | 7/1975 | McDonald | 128/2 F X |
| 3,909,363 | 9/1975 | Bucalo | 23/259 X |
| 3,929,412 | 12/1975 | Villari | 23/259 |
| 3,947,251 | 3/1976 | Quame | 23/259 |
| 4,000,649 | 1/1977 | Hanifl | 73/427 X |

Primary Examiner—Sidney Marantz
Attorney, Agent, or Firm—Darbo & Vandenburgh

[57] ABSTRACT

A cup-shaped receptacle is semi-surrounded by a shroud which is preferably integral with the receptacle and extends outwardly from the top thereof, then down in spaced relation to the sides of the receptacle to a plane level with or lower than the bottom of the receptacle. The rear of the shroud is open to permit access to the receptacle by the fingers of a person holding it, the rear opening being flanged to provide a shield to prevent spillage of urine upon the hand of the holder. The shroud is stiffly resilient and serves both as a shield against urine spillage and to stably support the cup upon a flat supporting surface.

10 Claims, 6 Drawing Figures

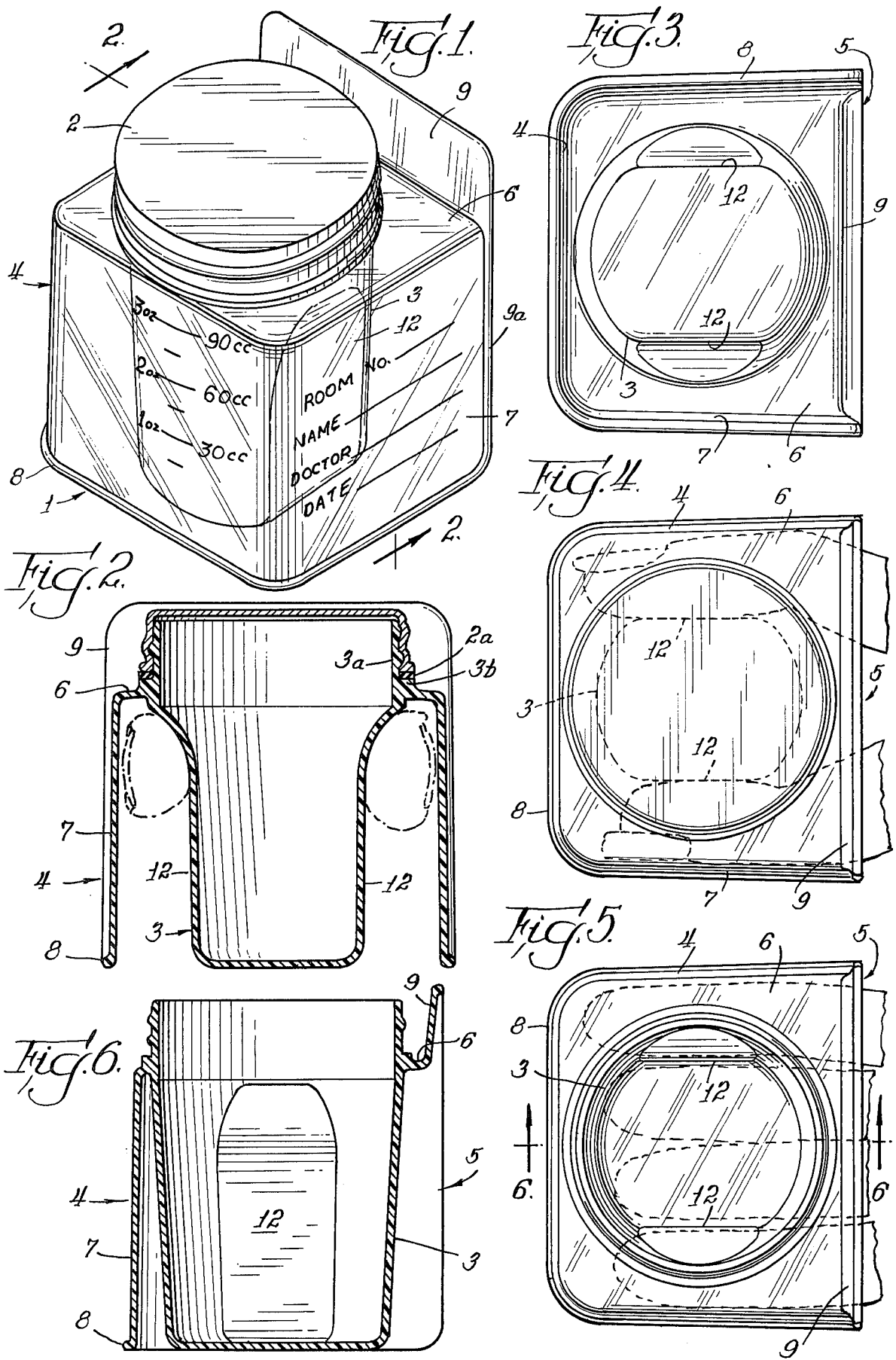

URINE SPECIMEN CONTAINER

BACKGROUND AND SUMMARY OF THE INVENTION

Urinalysis is a common procedure for diagnosis or monitoring of a patient's condition. The procedure has become routine in general physical examinations and large numbers of urine specimens are taken and analyzed or otherwise examined in hospital and clinical laboratories.

In producing the specimen, it is desirable that container means be provided which can be held and filled conveniently and which will shield the patient's hand against spillage and protect the sample against contamination. Since disease may be contracted from the urine of patients suffering from the disease, it is very important that the laboratory technician handling the specimen container be protected against spillage of the urine upon the skin. To guard against the hazard of spilling, the container should have a broad base so that it rests stably upon a supporting surface and is not easily tipped over.

Preferably, the specimen containers should be simple and inexpensive so that they may be discarded after a single use. The bodies and the caps should be nestable for convenient and efficient storage pending use.

Accordingly, it is an object of this invention to provide a patient urine specimen container which incorporates shielding to protect the hand of the patient while taking the sample and to protect the hands of laboratory technicians in handling the specimen. It is a further object to provide such a container which may be held securely in the hand by both the patient and the laboratory technician and which will rest stably upon a supporting surface.

Further objects and achievements of the invention will become apparent as the description thereof proceeds.

BRIEF DESCRIPTION OF THE DRAWING

In the accompanying drawing,

FIG. 1 is a perspective view showing the front, one side, and the top of the urine specimen container of the invention;

FIG. 2 is a cross-sectional view taken at the line 2—2 of FIG. 1;

FIG. 3 is a bottom view;

FIG. 4 is a top, plan view showing the closed container being held for removal of the screw cap;

FIG. 5 is a top, plan view showing the container with the cap removed and being held for filling, and FIG. 6 is a cross-sectional view taken at the line 6—6 of FIG. 5.

DESCRIPTION OF PREFERRED EMBODIMENT

The urine specimen container is a two-piece assembly comprising a multiple function but unitary base 1 and a screw cap 2. The plastic material is the relatively thin sections of the shroud 4 should be stiffly flexible; i.e., capable of "giving" under stress, like a leaf spring, not limp, so that the several portions of the container can serve to provide structural rigidity and also the springy finger-gripping action as hereinafter described.

The base of the specimen container comprises a cup-shaped urine receptacle 3 and a dual purpose shroud 4 which semi-surrounds receptacle 3, leaving an open rear 5 for lateral access to the receptacle 3. As is clearly seen in the sectional view, FIG. 2, the shroud, comprised of a top portion 6 extending outwardly from the mouth of the receptacle and a depending skirt 7, is spaced from the side walls of receptacle. The skirt portion of the shroud extends around the front and both sides of the container and terminates at its bottom in a horizontal stiffening flange 8. Preferably, the bottom surfaces of the receptacle 3 and flange 8 define a single plane for maximum stability of the specimen container when resting upon a flat surface. The plane of the flange should not be at a higher level than that of the bottom of the receptacle.

The rear of shroud 3 terminates in a flange 9 which extends across the top portion 6 of the shroud and downwardly at 9a along skirt 7 to flange 8. While flange 9 serves a stiffening function in the structure, its principal purpose is to provide a shield against urine spillage as will be explained hereinafter.

As is best seen in FIG. 2, the receptacle 3 is provided with a threaded mouth 3a at its top to receive screw cap 2 as a closure for the receptacle. A suitable gasket 2a is located upon shoulder 3b to ensure liquid-proof sealing of the closed receptacle.

Desirably, the opposite sides of receptacle 3 are indented somewhat as indicated at 12, FIG. 2, to provide space for the easy, but snug, insertion of the fingers of a person handling the specimen container as illustrated in FIG. 5 for filling the receptacle and in FIGS. 2 and 4 for handling the container with the urine specimen therein. (see FIG. 4) The space between the receptacle and the skirt portions of the shroud is thus augmented for finger access without making the overall container excessively wide.

As indicated in FIG. 1 of the drawing, provision may be made for the reception of specimen identification and other pertinent data on one side of the shroud. Also, as indicated in FIG. 1 the receptacle may be marked with volume and/or weight measurements for the convenience of the laboratory technician. Although shown on the front of the receptacle, these markings are preferably placed on the rear side of the receptacle where they can be read without looking through a thickness of the shroud.

ACHIEVEMENT

The urine specimen container as herein shown and described fully responds to the peculiar needs of a container for this service. In addition to the receptacle for the urine and a removable closure, the multi-faceted hazard of spillage is guarded against by several aspects of the design.

In the first stage of use, the container is literally inserted into the hand of the patient. As distinguished from merely picking up a simple specimen cup or jar, the container of the invention is pressed onto the fingers of the patient which form a yoke fitting tightly into the spaces between the receptacle and shroud and a bottom support. Once thus inserted, the container is held in position relative to the fingers and hand of the patient by the gripping action of the stiffly flexible plastic material so that a positive pull is necessary to withdraw the container from the fingers after deposit of the urine sample in the receptacle. The danger of slippage of the specimen container is substantially nil, both because the springy plastic skirt of the shroud grips the fingers and because the danger of making the surface of the receptacle slippery due to wetting by urine is avoided.

During the receptacle filling process, the shroud and rear flange shield the hand against the possibility that urine may be spilled upon it.

When the container is placed upon a flat surface, the relatively wide bottom of the shroud bearing upon the surface ensures a resting stability much greater than that of the cup alone. The hazard of accidental tipping is thus minimized. The stability of the container at rest and the certain facility with which the container may be held while the cap is screwed onto or off from the receptacle guard against another spillage hazard.

In the laboratory, the container must be held firmly while the cap is screwed off of the receptacle. Without the shroud, the grasping pressure applied directly to the thin-walled cup would tend to reduce the volume of the receptacle and possibly cause overflowing as the lid is removed. The shroud assists in holding the receptacle against turning or any movement that might result in spillage as the cup is being removed.

To transport the open container, the laboratory technician grasps the unit by inserting fingers, or a finger and thumb, into the spaces between the skirt portion of the shroud and the container. The hand is shielded against possible spillage and the resilient parts of the container which are engaged by the supporting fingers grip the fingers so that accidental slippage is most unlikely.

While these desirable functional features of the container structure, directed as they are to several types of hazards in the use of urine specimen containers, are somewhat complex, the container itself is simple and inexpensive and can justifiably be discarded after a single use.

I claim:

1. In a urine specimen container including a cup-shaped receptacle and a cap therefor, the improvement which comprises a shroud having a top portion extending outwardly from the top of the receptacle and a skirt portion depending from the periphery of said top portion across the front and along the two sides of the receptacle leaving the rear of the receptacle exposed, said skirt portion being spaced from the sides of the receptacle whereby fingers of a hand approaching the receptacle from the rear may pass under said shroud into the spaces on the respective sides of the receptacle to grasp and support the same while shielded by said shroud against the hazard of urine spillage.

2. A specimen container in accordance with claim 1 and including an upstanding flange extending across the top portion of the shroud at the rear thereof whereby to shield a hand supporting the receptacle from the rear thereof against the hazard of urine spillage.

3. A specimen container in accordance with claim 1 wherein the shroud is stiffly resilient and the skirt portion thereof is spaced from the receptacle at such a distance that fingers thrust into the respective spaces force the skirt portion resiliently outwardly whereby the fingers are gripped by the so stressed shroud and frictionally held in receptacle-supporting position.

4. A specimen container in accordance with claim 3 and including an upstanding flange extending across the top portion of the shroud at the rear thereof whereby to shield a hand supporting the receptacle from the rear thereof against the hazard of urine spillage.

5. A specimen container in accordance with claim 1 wherein the sides of the receptacle respectively opposite the respective sides of the shroud are indented to contribute a part of the space for the fingers.

6. A specimen container in accordance with claim 1 wherein the bottom edge of the skirt portion of the shroud defines a plane level with or lower than the bottom of the receptacle to enhance the stability of said container when resting upon a flat supporting surface.

7. A specimen container in accordance with claim 6 and including a flange extending outwardly from the bottom edge of the skirt portion of the shroud substantially in the plane thereof.

8. A urine specimen container comprising a cup-shaped receptacle having an open top adapted to receive a cap to close the same, a shroud having a top portion extending outwardly from the top of said receptacle and a skirt portion depending from the periphery of the top portion across the front and along the two sides of said receptacle leaving the rear of said receptacle exposed, said receptacle and said shroud being unitary and composed of thin stiffly resilient plastic material, said skirt portion being spaced from the sides of said receptacle whereby fingers of a hand approaching said receptacle from the rear may pass under said shroud into the spaces on the respective sides of said receptacle to grasp and support the same, and an upstanding flange extending across the top portion of said shroud as the rear thereof to provide with said shroud a shield against the hazard of urine spillage.

9. A urine specimen container in accordance with claim 8 wherein the bottom edge of the skirt portion of the shroud defines a plane level with or lower than the bottom of the receptacle to enhance the stability of said container when resting upon a flat supporting surface.

10. A urine specimen container in accordance with claim 9 and including a flange extending outwardly from the bottom edge of the skirt portion of the shroud substantially in the plane thereof.

* * * * *